United States Patent
Beckerman (10) Patent No.: US 10,342,391 B2
(45) Date of Patent: Jul. 9, 2019

(54) BOTTLE HOLDER

(71) Applicant: COLGATE-PALMOLIVE COMPANY, New York, NY (US)

(72) Inventor: Scott Beckerman, South Orange, NJ (US)

(73) Assignee: Colgate-Palmolive Company, New York, NY (US)

( * ) Notice: Subject to any disclaimer, the term of this patent is extended or adjusted under 35 U.S.C. 154(b) by 46 days.

(21) Appl. No.: 15/366,602

(22) Filed: Dec. 1, 2016

(65) Prior Publication Data

US 2018/0153354 A1 Jun. 7, 2018

(51) Int. Cl.
| | |
|---|---|
| A47K 5/18 | (2006.01) |
| A47F 1/08 | (2006.01) |
| A47K 5/12 | (2006.01) |
| B05B 11/00 | (2006.01) |

(52) U.S. Cl.
CPC ............... *A47K 5/18* (2013.01); *A47F 1/085* (2013.01); *A47K 5/1211* (2013.01); *B05B 11/0054* (2013.01); *B05B 11/30* (2013.01); *A47K 5/1205* (2013.01); *A47K 2201/02* (2013.01); *A61C 2202/02* (2013.01)

(58) Field of Classification Search
CPC ......... A47K 5/18; A47K 5/1211; A47F 1/085; B05B 11/0054; B05B 11/30
USPC .... 222/153.03, 180–184, 608–612; 248/313, 248/154
See application file for complete search history.

(56) References Cited

U.S. PATENT DOCUMENTS

| | | | | |
|---|---|---|---|---|
| 2,883,139 | A * | 4/1959 | Dobkin | A47J 47/16 248/311.2 |
| 4,213,592 | A * | 7/1980 | Lingenfelser | A62C 13/78 248/313 |
| 4,615,476 | A | 10/1986 | Hobbs et al. | |
| 5,713,492 | A | 2/1998 | DeGennaro | |
| 6,041,974 | A | 3/2000 | Poitras et al. | |
| 6,820,770 | B2 * | 11/2004 | Makino | A47K 5/12 222/180 |
| 7,188,629 | B2 | 3/2007 | Mehes et al. | |
| D620,735 | S | 8/2010 | Schmidt et al. | |
| 8,668,178 | B2 * | 3/2014 | Ziaylek | F17C 13/084 224/570 |
| 9,155,428 | B2 * | 10/2015 | Haworth | A47K 5/12 |

(Continued)

OTHER PUBLICATIONS

International Search Report and Written Opinion of the International Searching Authority in International Application No. PCT/US2017/063657, dated Feb. 14, 2018.

(Continued)

*Primary Examiner* — Lien M Ngo (57) ABSTRACT

A fluid dispenser for dispensing a fluid and a method for dispensing a fluid such as a mouthwash may include a container having an internal reservoir for containing a volume of the fluid and a fluid pump connected to the container. The fluid pump may include a head, a spout, a stem, and a collar. The collar may attach the fluid pump to the container. The fluid dispenser may further include a container holder having a stem support that defines a slot that receives the stem of the fluid pump, a base, and an attachment member extending from the stem support toward the base. Various fluid dispenser designs, implementations, and uses are discussed.

12 Claims, 7 Drawing Sheets

(56) References Cited

U.S. PATENT DOCUMENTS

| | | | | |
|---|---|---|---|---|
| 2004/0149765 A1* | 8/2004 | Pryce | ............... | A47F 7/283 |
| | | | | 220/737 |
| 2012/0181405 A1* | 7/2012 | Zlatic | ............... | A47G 23/0225 |
| | | | | 248/313 |
| 2013/0076514 A1* | 3/2013 | Wegelin | ............... | B05B 11/308 |
| | | | | 340/573.1 |
| 2014/0001211 A1 | 1/2014 | Thomas et al. | | |
| 2016/0288151 A1* | 10/2016 | Schultz | ............... | F16M 11/105 |

OTHER PUBLICATIONS

Internet Download: http://reneestoll.blogspot.com/2013/09/sao-paulo-churiscaria.html, Retrieved from the internet on Oct. 21, 2016, 1 page.

Got Fresh Breath, "Mouthwash Dispenser Mini (White)—For GotFreshBreath Alcohol-Free Mouthwash", https://www.amazon.com/dp/B00H88G90C/?tag=heatipforabea-20&th=1, Retrieved from the internet on Oct. 24, 2016, pp. 1-6.

"1200ml Satin stainless steel mouth wash dispenser with cup dispenser,manual mouthwash dispenser", http://aytcn.en.alibaba.com/product/60032095304-0/1200ml_Satin_stainless_steel_mouth_wash_dispenser_with_cup_dispenser_manual_mouthwash_dispenser.html, Retrieved from the internet on Oct. 24, 2016, pp. 1-8.

Internet Dowload: http://www.bbc.com/news/business-30416226, Retrieved from the internet on Nov. 10, 2016, 1 page.

* cited by examiner

BOTTLE HOLDER

BACKGROUND

This section provides background information related to the present disclosure which is not necessarily prior art.

Daily oral hygiene is important in reducing or preventing the occurrence of tooth decay, gum disease, halitosis, and other undesirable oral and dental conditions. Oral care most frequently includes the use of a toothbrush and toothpaste, dental floss, and/or mouthwash or oral rinse (hereinafter collectively, "mouthwash") in a home environment. The frequency of oral hygiene may decrease while at work and in other public places due, in part, to the unavailability of necessary products. Transporting oral care products is an inconvenience that most individuals avoid in favor of performing the necessary hygiene at home.

In particular, the frequent use of mouthwash may be effective in reducing or preventing tooth decay and gingivitis, reducing plaque and the formation of tartar, as well as freshening breath. However, transporting and storing a sufficient quantity of mouthwash in a work or public environment is inconvenient and requires planning.

Locking containers for storing and dispensing mouthwash have been proposed. For example, U.S. Pat. No. 5,713,492 describes a mouthwash dispensing device including first and second reservoirs adapted to contain mouthwash therein. The mouthwash dispensing device includes a lock assembly to prevent unauthorized access to the interior of the device.

Containers for storing and dispensing mouthwash may generally include moving structures that are integral to the dispenser that may fail over time from use. Further, refilling the dispensers may require substantial time and can result in spillage of the mouthwash. The internal structures of dispensers may contact the mouthwash therefore require periodic cleaning and other maintenance.

A mouthwash bottle holder that that overcomes one or more problems with prior dispensers would be a welcome addition to the art.

BRIEF SUMMARY

The following presents a simplified summary in order to provide a basic understanding of some aspects of the present teachings. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later.

A fluid dispenser according to the present teachings includes a container having an internal reservoir for containing a volume of the fluid and a fluid pump received by the container. the fluid pump includes a head, a spout, a stem, and a collar, wherein the collar attaches the fluid pump to the container. The fluid dispenser further includes a container holder having a stem support that defines a slot that receives the stem of the fluid pump, a base, and an attachment member extending from the stem support toward the base.

The fluid dispenser may optionally include a first surface having a hole therein that receives a bottom portion of the container, and a second surface that extends away from the first surface. The bottom portion of the container received by the hole in the first surface may be configured to physically contact a platform upon which the fluid dispenser is positioned during use. The first surface may be supported by the second surface and configured to be free from physical contact with the platform upon which the fluid dispenser is positioned during use.

A height of the attachment member may be designed such that a distance from an underside of the stem support to a bottom edge of the second surface is essentially equal to a distance from a bottom surface of the container to a top surface of the collar.

In an implementation, the base may include a first surface and a second surface that extends approximately perpendicular to the first surface. The stem support may be directly connected to the attachment member, the attachment member may be directly connected to the first surface of the base, and the first surface of the base may be directly connected to the second surface of the base. The stem support may further include a recess therein and the fluid dispenser may further include an insert configured to be received by the recess in the stem support such that the insert blocks the slot of the stem support.

Optionally, the stem support may further include a recess therein, and the fluid dispenser may further include a locking mechanism. The locking mechanism may include an insert configured to be received by the recess in the stem support such that the insert blocks the slot of the stem support, and a closure that extends through the insert and the stem support.

In an implementation, the a locking mechanism may include an insert configured to be received by the recess in the stem support such that the insert blocks the slot of the stem support, a post that extends through the stem support and the insert, a lock portion that receives the post, and a key configured to be inserted into the lock portion to lock and unlock the lock portion from the post.

In another implementation, the fluid dispenser may optionally include an arm having a first end, a second end opposite the first end, and a void within the second end. The fluid dispenser may further include a channel that extends through the stem support and first end of the arm, and a spindle extending through the channel that attaches the first end of the arm to the stem support. The arm may be rotatable about the spindle. The stem support may further include a protrusion, where the void is configured to receive the protrusion, and the arm may be configured to block the slot in the stem support when the protrusion is positioned within the void in the arm.

Optionally, the container holder may include a transverse plate having a hole therein that receives a bottom portion of the container and the base may further include a front plate and a bottom plate. The stem support may be directly connected to the attachment member, the attachment member may be directly connected to the transverse plate, the transverse plate may be is directly connected to the front plate of the base, and the front plate may be directly connected to the bottom plate. The container may physically contact the bottom plate when the container is positioned in the hole. A height of the attachment member, a height of the transverse plate, and a height of the front plate may be designed such that a distance from an underside of the stem support to a top of the bottom plate is essentially equal to a distance from a bottom surface of the container to a top surface of the collar. Optionally, the attachment member may be further directly connected to the bottom plate of the base. The fluid dispenser may optionally include a volume of mouthwash or mouth rinse contained within the internal reservoir of the container.

Container holder may be formed from a single continuous piece of material that includes at least one of a polymer and a metal. The container holder may be a single continuous piece of injection-molded polymer.

In an implementation, the fluid dispenser may optionally include an accessory plate extending from the attachment member and a cup dispenser attached to the accessory plate.

In another implementation, a container holder for holding a container includes a stem support that defines a slot configured to receive a stem of a fluid pump, where the slot is configured for insertion of the stem into the slot in a lateral direction. The container holder further includes a base and an attachment member extending from the stem support toward the base.

The container holder may further optionally include a transverse plate having a hole therein configured to receive bottom portion of a container. The base may further include a front plate and a bottom plate, and the stem support may be directly connected to the attachment member. Additionally, the attachment member may be directly connected to the transverse plate, the transverse plate may be directly connected to the front plate of the base, the front plate may be directly connected to the bottom plate, and the container may physically contact the bottom plate when the container is positioned in the hole. The attachment member may be directly connected to the bottom plate of the base.

Further, optionally, the stem support may further include a recess therein and the container holder may further include an insert configured to be received by the recess in the stem support such that the insert blocks the slot of the stem support.

The container holder may further include a first surface having a hole therein that receives a bottom portion of a container and a second surface that extends away from the first surface. The bottom portion of the container received by the hole in the first surface may be configured to physically contact a platform upon which the fluid dispenser is positioned during use. The first surface may be supported by the second surface and may be configured to be free from physical contact with the platform upon which the fluid dispenser is positioned during use.

A method for containing a volume of fluid includes placing a bottom portion of a container within a hole defined by a container holder, inserting a stem of a pump within a slot in a stem support of the container holder, and positioning the stem support between a head of the pump and a collar of the pump, wherein the positioning prevents the container from being removed from the container holder in a direction directly away from a base of the container holder. The method further includes placing an insert into a recess within the stem support, thereby blocking removal of the stem of the pump from the slot. The insert is locked within the recess using a locking mechanism.

Further areas of applicability of the present invention will become apparent from the detailed description provided hereinafter. It should be understood that the detailed description and specific examples, while indicating some preferred aspects of the invention, are intended for purposes of illustration only and are not intended to limit the scope of the invention.

BRIEF DESCRIPTION OF THE DRAWINGS

The present invention will become more fully understood from the detailed description and the accompanying drawings, which are incorporated in, and constitute a part of this specification and illustrate aspects of the present teachings. Together with the description, the figures serve to explain the principles of the disclosure, wherein.

It should be noted that some details of the figures have been simplified and are drawn to facilitate understanding of the present teachings rather than to maintain strict structural accuracy, detail, and scale.

DETAILED DESCRIPTION

The following description of various preferred aspects is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

One or more aspects of a mouthwash bottle holder in accordance with the present teachings may provide a low-cost mouthwash dispenser that allows for simplified replacement or refilling of a depleted dispenser compared to some conventional dispenser designs. The bottle holder may reduce the chance that the mouthwash bottle moves, falls, spills, is tampered with, or is stolen. The holder may be designed for a bottle including a corresponding pump. The size and shape of the mouthwash bottle holder may be modified to accommodate different pumps and scaled to fit larger or smaller bottles. The mouthwash bottle holder may include a locking mechanism to secure the mouthwash bottle within the holder, for example in a public or semi-private area such as a public or semi-private washroom to prevent theft. Further, the locking mechanism may secure a pump onto the bottle to prevent removal of the bottle and pump, and to inhibit tampering with the mouthwash within the bottle.

While various examples of designs are described and depicted herein, it will be appreciated that a mouthwash bottle holder may include other structures and/or design features that have not been depicted for simplicity, while one or more depicted structures and/or design features may be removed or modified.

Figure 1:
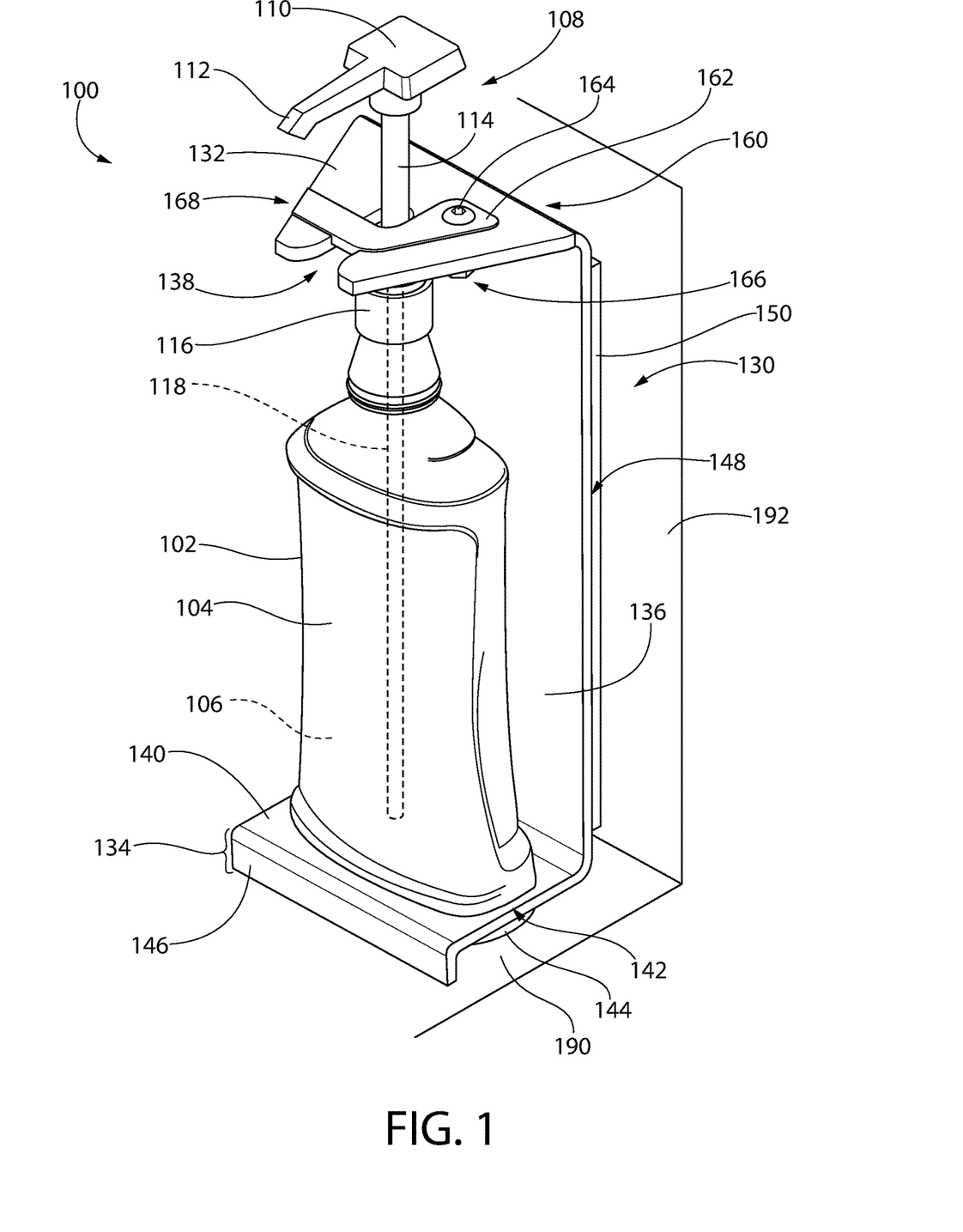
FIG. 1 is a perspective depiction of a fluid dispenser such as a mouthwash dispenser in accordance with an implementation of the present teachings.

FIG. 1 is a perspective depiction of a mouthwash dispenser 100 according to one implementation of the present teachings. The mouthwash dispenser 100 of FIG. 1 includes a container 102 such as a bottle having an internal reservoir 104 for storing a volume of mouthwash 106. The mouthwash dispenser 100 may further include a pump 108 having a head 110, a spout 112, a stem 114, a collar 116, and a hollow tube 118 that extends into the mouthwash 106 within the container 102. The collar may be a threaded collar that attaches the fluid pump to the container with container threads (collar threads and container threads not depicted for simplicity). The parts, operation, and attachment of a pump to dispense a fluid from a container are well known.

The mouthwash dispenser 100 of FIG. 1 further includes a holder 130 that is configured to support and position the container 102 and the pump 108 during use. The holder 130 may include a stem support 132, a base 134, and an attachment member 136. The attachment member 136 may extend away from the stem support 132 at an angle, for example, a right angle, and toward the base 134. In this design, the attachment member 136 further extends vertically between the stem support 132 and the base 134, and spans the entire region from the stem support 132 to the base 134. The holder 130 may be formed from a single continuous piece of material such as injection-molded, thermoformed, or three-dimensional (3D) printed polymer such as plastic, a metal such as aluminum or stainless steel, carbon fiber, or another suitable material. Material thickness is determined, at least in part, by the size of the holder and the composition of the material selected for manufacture. In another implementation, the holder 130 may be formed from two or more separate parts that are bolted or welded together, or attached using an adhesive or other fastener, or otherwise connected.

The stem support 132 may define a slot 138 that receives the stem 114 of the pump 108. The slot 138 may be open at a front (e.g., opposite the attachment member 136) or a side of the stem support 132, and thereby configured for insertion of the stem 114 of the pump 108 into the slot 138 in a lateral or horizontal direction such that the stem support 132 is positioned between the head 110 and the collar 116 of the pump 108. When so positioned, the stem support 132 prevents removal of the pump 108 and the container 102 in a direction substantially away from the first surface 140 of the base 134 (e.g., in an upward direction as depicted in FIG. 1). For example, during use, the stem support 132 prevents the pump 108 and the container 102 from being removed from the holder 130 in a vertical direction because the stem support 132 physically contacts the collar 116 of the pump 108.

The base 134 may include a first surface or support 140 that defines a hole 142 that receives a bottom portion 144 of the container 102. The base 134 may further include a second surface or support 146 that that extends away from the first surface 140 at a right angle or an oblique angle. In this implementation, the bottom portion 144 of the container 102 may extend through the hole 142 in the first surface 140 and physically contact or rest on a platform 190 such as a counter 190, for example a horizontal surface or counter 190, upon which the dispenser 100 rests during use. The edge of the second surface 146 may also contact or rest on the counter 190 such that the first surface 140 is supported by the second surface 146 and may therefore be free from physical contact with the counter 190 during use.

The attachment member 136 may extend between the stem support 132 and the base 134 in a vertical direction as depicted. The stem support 132 and the first surface 140 of the base 134 may extend away from the attachment member 136 at right angles, or another suitable angle. A height of the attachment member 136 from the stem support 132 to the first surface 140 of the base 134 may be designed such that the pump 108 cannot be removed from the container 102 while positioned within the slot 138 in the stem support 132. Additionally, the bottom portion 144 of the container 102 may be tapered such that it will extend into the hole 142 in the first surface 140 only a limited distance to prevent removal of the container 102 through the hole 142. Thus a height of the attachment member 136 is designed such that a distance from the underside of the stem support 132 to the bottom edge of the second surface 146 (i.e., the edge of the second surface 146 that may contact the counter 190) is essentially equal to a distance from a horizontal bottom surface of the container 102 to a top surface of the collar 116. This, along with the locking mechanism 160, assists in preventing the container 102 from being removed from the holder 130 and prevents the collar 116 of the pump 108 from being unscrewed or otherwise removed from the container 102, and prevents removal of the container 102 and pump 108 from the holder 130.

During use, a back surface 148 of the attachment member 136 may be attached to a vertical surface 192 such as wall or mirror 192 that may intersect the platform 190. The attachment member 136 may be attached to the wall or mirror 192 using a fastener 150 such as a double-sided pressure adhesive, one or more bolts or screws, or another suitable fastener 150. The fastener 150 secures the holder 130 to the wall or mirror 192 to deter removal or theft of the holder 130.

Figure 2:
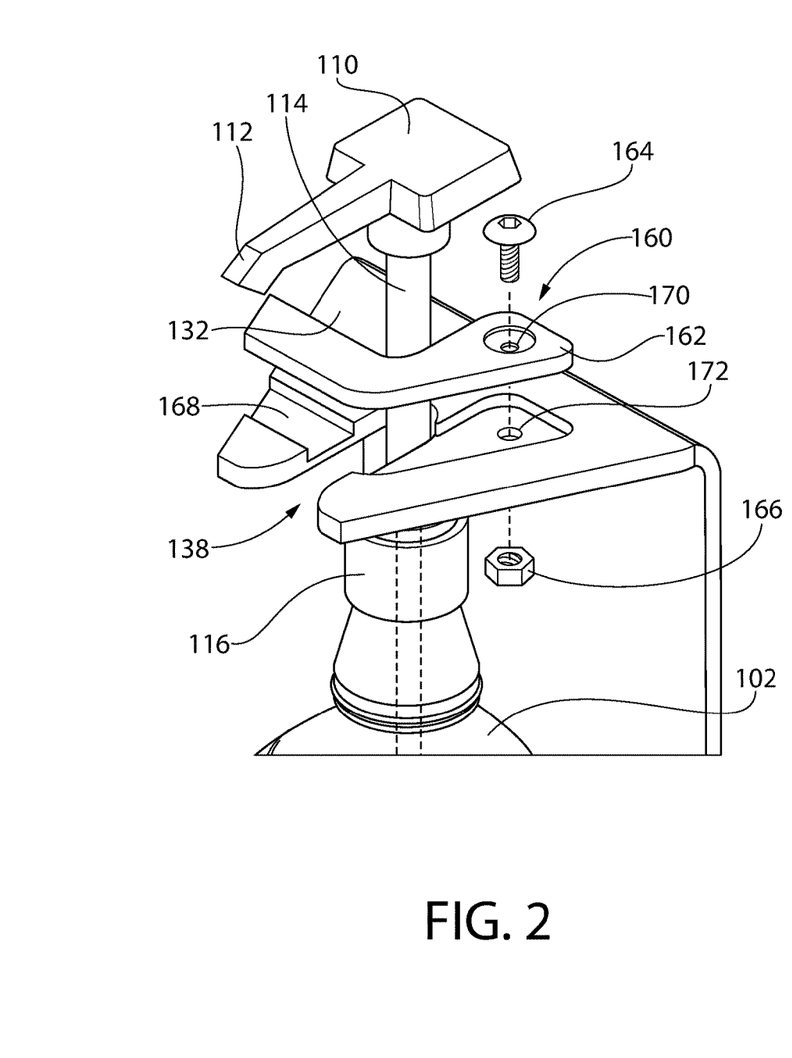
FIG. 2 is an exploded perspective depiction of detail of an optional locking mechanism in accordance with an implementation of the present teachings.

FIG. 1 further depicts an optional lock assembly 160 (i.e., lock, locking mechanism) that may deter removal, theft, and/or tampering of the container 102, mouthwash 106 and/or pump 108. An optional lock as described herein may be used with any holder disclosed herein. FIG. 2 is an exploded view depicting the details of the lock assembly 160 of FIG. 1. The lock assembly 160 of the FIG. 1 and FIG. 2 implementation includes an insert 162, a bolt 164, and a nut 166, where the bolt 164 and the nut 166 affix or attach the insert 162 to the stem support 132. In other implementations, the insert 162 may be attached to the stem support 132 by another type of closure that extends through the insert 162 and the stem support 132, such as a partially threaded machine screw that threads into a threaded hole (e.g., hole 172) in the stem support 132, or the like. The stem support 132 may include a recess 168 that is configured to receive the insert 162. For example, the recess 168 may be correspond to, or be coextensive with, the insert 162 when the insert 162 is positioned within the recess 168 as depicted in FIG. 1. As depicted, the recess 168 may generally have a perimeter that is congruent with a perimeter of the insert 162 and the recess 168 may be present on both sides of the slot 138, as depicted. The insert 162 may be received by the recess 168 with little lateral movement of the insert 162 within the recess 168 and thus the insert 162 cannot be rotated so as not to block the slot 132 when the insert 162 is seated in the recess 168.

After the stem 114 of the pump 108 is inserted into, positioned within, and/or received by the slot 138 in the stem support 132, the insert 162 may be inserted into, positioned within, and/or received by the recess 168. As depicted, when seated within the recess 168, the insert 162 extends across and blocks the slot 138, thereby blocking removal of the stem 114 of the pump 108 from the slot 138. To secure or lock the insert 162 within the recess 168, the bolt 164 of the locking mechanism 160 may be placed through a first hole 170 in the insert 162 and through a second hole 172 in the stem support 132, where the first hole 170 and the second hole 172 are vertically aligned. Subsequently, the nut 166 may be threaded onto the bolt 164. The bolt 164 may be tightened onto the nut 166 using a screwdriver or another appropriate tool. For example, for improved security, the bolt 164 may have a hex head, a Torx® head, or another non-standard head such that a non-standard tool such as a hex key, a Torx key, or another suitable non-standard tool is required for removal of the bolt 164 and nut 166 from the insert 162 and the stem support 132. The bottom portion 144 of the container 102 is inserted through the hole 142 in the first surface 140, which prevents tilting or angling the bottom end of the container 102 so as to remove the container from the holder 130. Similarly, the insert 162 prevents tilting or angling the top end of the container 102 and the pump 108 so as to remove the stem 114 of the pump 108 from the stem support 132. As noted previously, the stem support 132 and the insert 162 also block and prevent the collar 116 of the pump 108 from being unscrewed or otherwise removed from the container 102. Thus the container 102 and pump 108 are secured within the holder 130.

Figure 3:
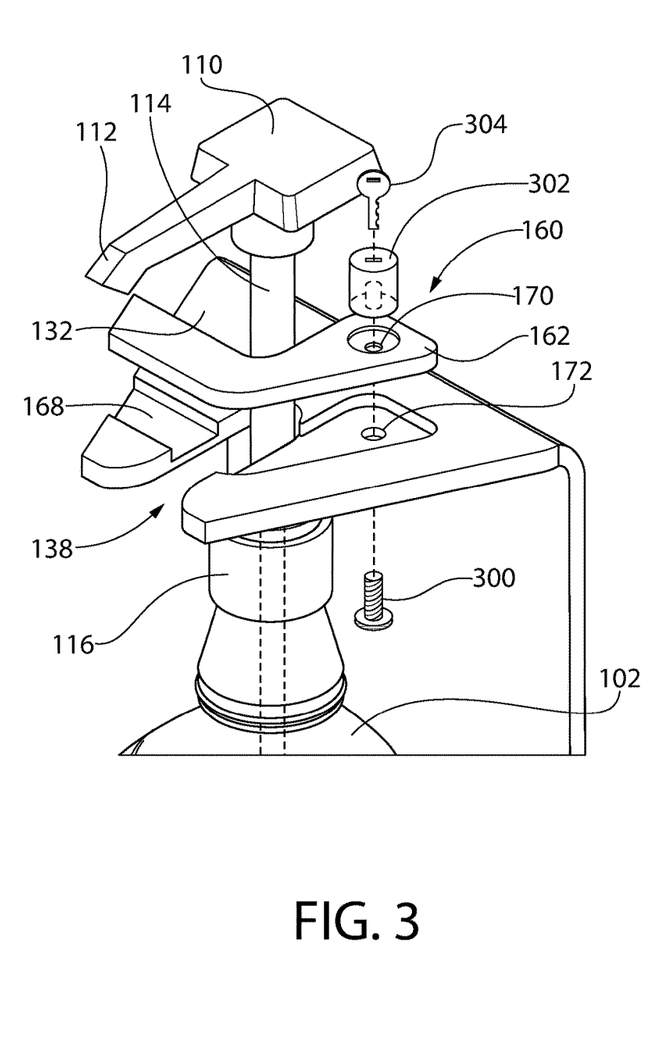
FIG. 3 is an exploded perspective depiction of detail of another optional locking mechanism design in accordance with an implementation of the present teachings.

It will be appreciated that other means or techniques for securing the insert 162 to the stem support 132, for example a keyed lock such as that depicted in FIG. 3, may be used for increased security. FIG. 3 depicts a pin- or receiver-style lock including a post 300, a lock portion 302, and a key 304. During use, the post 300 may be inserted to extend through the hole 172 in the stem support 132 and the hole 170 in the insert 162. The post 300 may then be inserted to extend into the lock portion 302 such that the lock portion 302 receives the post 300. The post 300 may include threads that are threaded onto threads within the lock portion 302, and then the lock portion 302 may be locked onto, and unlocked from, the post 300 using the key 304. Other keyed lock styles are contemplated.

Figure 4:
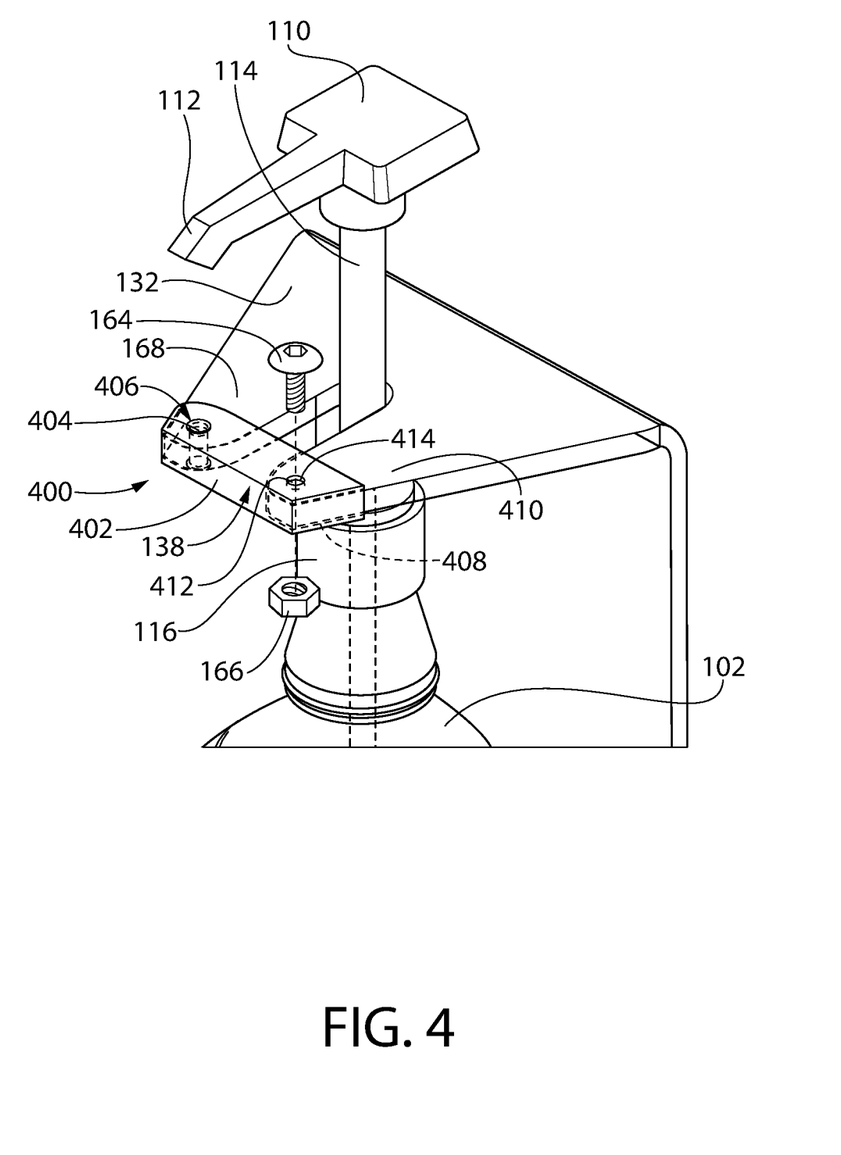
FIG. 4 is an exploded perspective depiction of detail of another optional locking mechanism design in accordance with an implementation of the present teachings.

FIG. 4 depicts another design for a locking mechanism 400 that allows the pump 108 and container 102 to be secured within the holder 130 by blocking the slot 138. This implementation includes an arm 402 that may be pivoted or is rotatable, for example, about a spindle 404 that extends through a channel 406 within a first end of the arm 402 and the stem support 132, and attaches the first end of the arm 402 to the stem support 132. The spindle 404 may include upper and lower flanges inset into the surface of the arm 402 that inhibit removal of the spindle 404. The arm 402 may define a void 408 at a second end of the arm 402 that is opposite the first end of the arm 402. The void 408 receives a protrusion 410 of the stem support 132, such that a hole 412 through the second end of the arm 402 is vertically aligned with a hole 414 in the protrusion 410 of the stem support 132. The arm 402 may be secured to block the slot 138 using a bolt 164 that extends through the holes 412, 414, and a nut 166 that attaches to the bolt 164. An exemplary bolt 164 and nut 166 are described in more detail above, and other fasteners, such as the post 300, lock 302, and key 304 of FIG. 3, or other locking mechanisms, are contemplated.

The holder 130 in the FIG. 1 implementation includes the attachment member 136 that extends perpendicularly from the stem support 132 to the first surface 140 of the base 134. When using an adhesive as the fastener 150, the adhesive may substantially cover the entire back surface 148 of the attachment member, thereby providing a large adhesive surface area and a secure connection to the wall or mirror 192 that is difficult for a thief or vandal to remove. Further, the base 134 includes the hole 142 that receives the bottom portion 144 of the container 102, and the bottom portion 144 of the container 102 may rest on the counter 190. In various implementations, the holder 130 may be formed from a single continuous piece of polymer such as an impact-resistant plastic or a single continuous piece of metal. To replace a depleted supply of the mouthwash 106, the optional lock assembly 160, if used, may be removed using the key 304 (FIG. 3) or a tool suitable for the specific design of the bolt 164 (FIG. 2). The stem 114 may be pulled away from the stem support 132 through the slot 138, thus tilting the top end of the container 102 away from the attachment member 136 and the wall or mirror 192. Once the stem 114 is removed from the slot 138 in the stem support 132, the container 102 and pump 108 may be lifted such that the bottom portion 144 of the container 102 is removed from the hole 142 in the first surface 140 of the base 134. The pump 108 may be removed from the container 102, such as by unscrewing the collar 116, and reused on a new container, or the container 102 may be refilled with mouthwash 106 and the pump 108 may be replaced on the container 10, or the entire container 102 and pump 108 may be replaced with a new container and pump. After replenishment or replacement, the container 102 and pump 108 may be replaced in the holder 130 and secured using the lock assembly 160 as previously described. Various prior dispensers have dispensing mechanisms that are integral to the dispenser and holder and thus must always be reused. Such prior dispensers eventually suffer dispenser failure, which causes a difficult removal of the entire dispenser/holder, which may be secured to a wall or counter, and which is avoided by dispensers in accordance with the present disclosure. Such prior dispensers may also require maintenance and cleaning that is not required by dispensers in accordance with the present disclosure, as replacing the entire container and pump mechanism in accordance with implementations of the present disclosure may reduce failures, cleaning, and maintenance.

Figure 5:
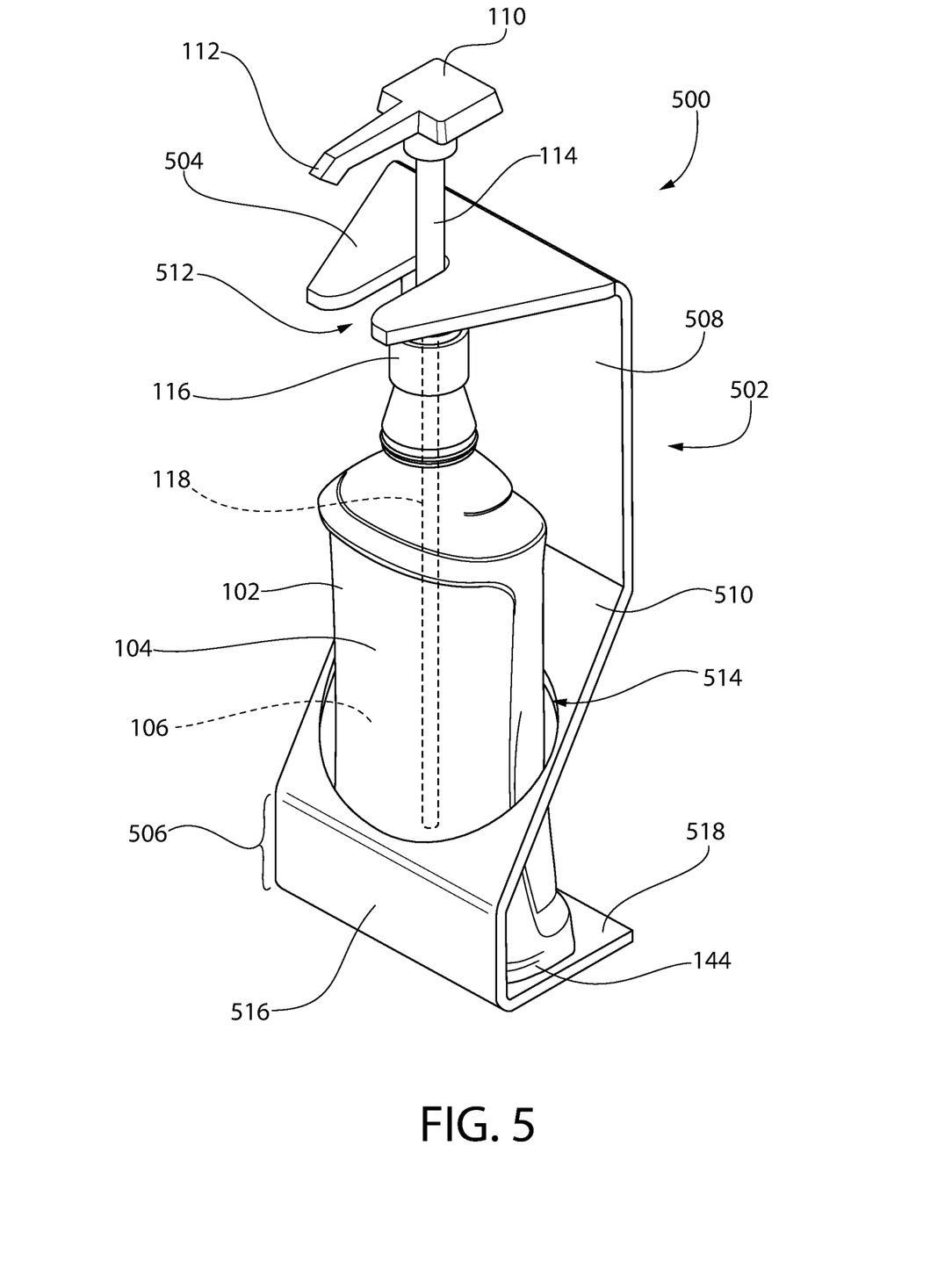
FIG. 5 is a perspective depiction of fluid dispenser in accordance with another implementation of the present teachings.

FIG. 5 depicts another design of a mouthwash dispenser 500 in accordance with the present teachings. The mouthwash dispenser 500 includes a holder 502 that may be formed from a single continuous piece of material such as injection-molded or 3D printed polymer such as plastic, a metal such as aluminum or stainless steel, or another suitable material. In another implementation, the holder 502 may be formed from two or more separate parts that are bolted or welded together, or attached using an adhesive or other fastener. FIG. 5 does not depict an optional locking mechanism, although the use of a locking mechanism, as described above, with the dispenser of FIG. 5, or other dispensers in accordance with the teachings herein, is contemplated.

The holder 502 includes a stem support 504, a base 506, an attachment member 508, and a transverse plate 510. The stem support 504 includes a slot 512 that receives the stem 114 during use of the dispenser 500. The attachment member 508 may extend away from the stem support 504 at an angle, for example, a right angle, and toward the base 506. In this design, the attachment member 136 further extends perpendicularly between the stem support 504 and the base 134, from the stem support 504 to the transverse plate 510. The transverse plate 510 extends from the attachment member 508 to the base 506 at an oblique angle relative to the attachment member 508. The transverse plate 510 defines a hole 514 therein that receives the container 102. The base 506 includes a vertically oriented front plate 516 and a horizontally oriented bottom plate 518 that intersects or connects to the front plate 516. During use, the bottom portion 144 of the container 102 rests on the bottom plate 518. The transverse plate 510 is thus connected to the attachment member 508 at a back of the dispenser 500 and to the front plate 516 at a front of the dispenser 500.

To replace a depleted supply of mouthwash 106, the stem 114 may be pulled or tilted away from the stem support 504 and the attachment member 508 through the slot 512. Once the stem 114 is removed from the slot 138 in the stem support 132, the container 102 and pump 108 may be lifted such that the bottom portion 144 of the container 102 is removed from the hole 514 in the transverse plate 510. As described previously, after the container 102 with the pump 108 is removed from the holder 502, the pump 108 may be removed from the container 102 and reused on a new container, or the entire container 102 and pump 108 may be replaced with a new container and pump.

In FIG. 1, the edges of the first surface 140 that define the hole 142 may physically contact the container 102 near the bottom of the container 102. Compared to the holder 130 of FIG. 1, the edges of the transverse plate 510 that define the hole 514 of FIG. 5 may physically contact the container 102 higher and closer to the middle portion of the container 102, such that the contact point(s) are closer to the center of gravity of the container 102, compared to the contact points of the holder 130. For various implementations of holders that do not include the optional locking assembly 160, physically contacting the container 102 at a higher point nearer to its center of gravity may reduce accidental forward tipping of the container 102, such as during use of the pump 108.

In the FIG. 5 structure, the stem support 504 is directly connected to the attachment member 508, the attachment member 508 is directly connected to the transverse plate 510, the transverse plate 510 is directly connected to the front plate 516 of the base 506, and the front plate 516 is directly connected to the bottom plate 518 of the base 506.

Additionally, heights of the attachment member 508, the transverse plate 510, and the front plate 516 are designed such that a distance from the underside of the stem support 504 to the top of the bottom plate 518 is essentially equal to a distance from a bottom horizontal surface of the container 102 to a top surface of the collar 116. This, along with a locking mechanism, assists in preventing the container 102 from being removed from the holder 502 and prevents the collar 116 of the pump 108 from being unscrewed or otherwise removed from the container 102, and prevents removal of the container 102 and pump 108 from the holder 502.

Figure 6:
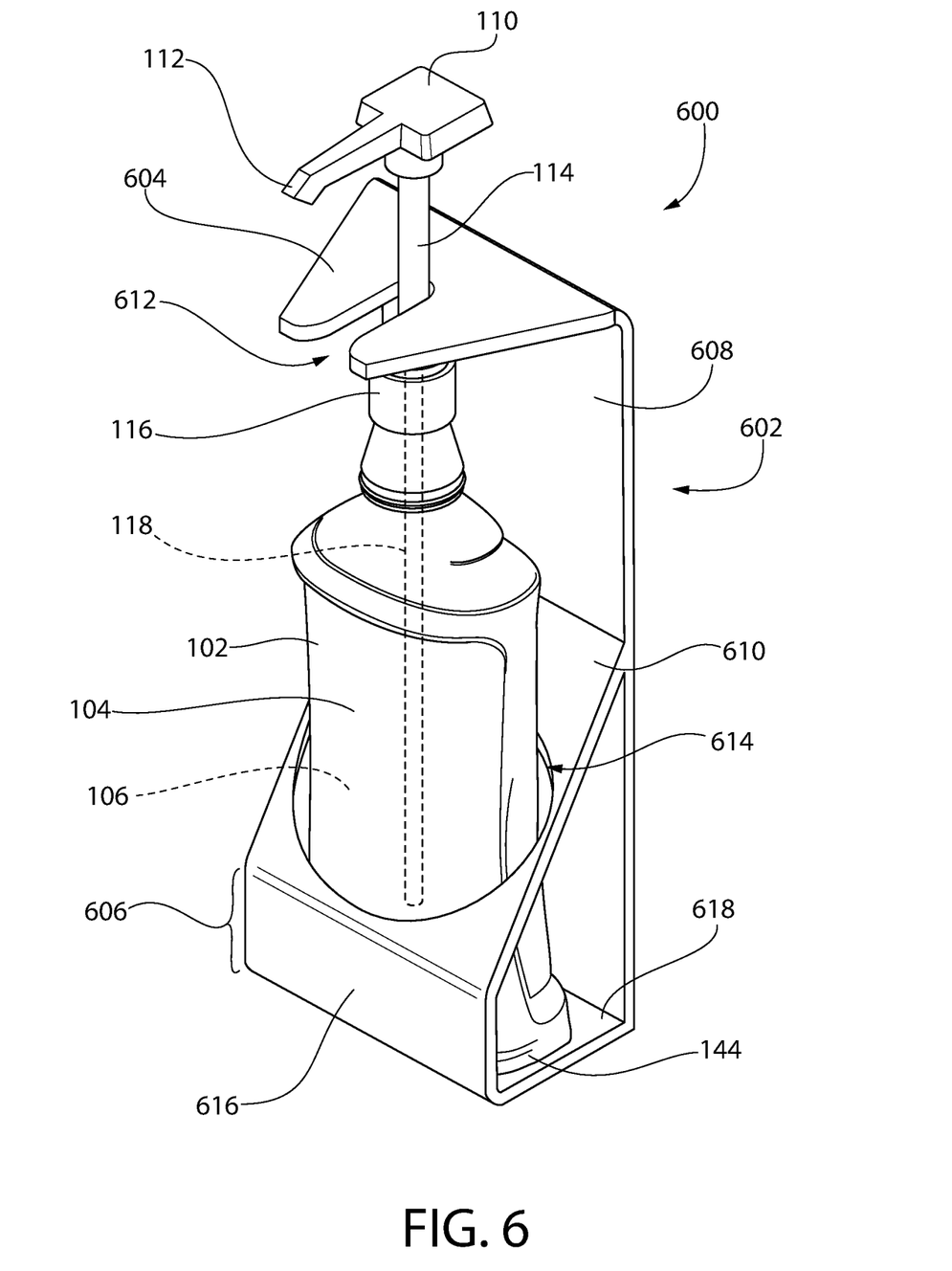
FIG. 6 is a perspective depiction of fluid dispenser in accordance with another implementation of the present teachings.

FIG. 6 depicts another design of a mouthwash dispenser 600 in accordance with the present teachings. The mouthwash dispenser 600 includes a holder 502 that may be formed from a single continuous piece of material such as injection-molded or 3D printed polymer such as plastic, a metal such as aluminum or stainless steel, or another suitable material. In another implementation, the holder 602 may be formed from two or more separate parts that are bolted or welded together, or attached using an adhesive or other fastener. FIG. 6 does not depict an optional locking mechanism, although the use of a locking mechanism as described above, with the dispenser of FIG. 6, or other dispensers in accordance with the teachings herein, is contemplated.

The holder 602 includes a stem support 604, a base 606, an attachment member 608, and a transverse plate 610. The stem support 604 includes a slot 612 that receives the stem 114 during use of the dispenser 600. The attachment member 608 may extend away from the stem support 604 at an angle, for example, a right angle, and toward and physically contacting the base 606 and, more specifically, a horizontally oriented bottom plate 618 of the base 606. In this implementation, the attachment member 608 further extends perpendicularly between the stem support 604 and the base 606, and more specifically from the stem support 604 to the bottom plate 618. The transverse plate 610 extends from an area near the middle of the attachment member 608 to the base 606 at an oblique angle relative to the attachment member 608. The transverse plate 610 defines a hole 614 therein that receives the container 102. The base 606 includes a vertically oriented front plate 616 as well as the horizontally oriented bottom plate 618. The bottom plate 618 intersects and connects to the front plate 616, for example, at a right angle. During use, the bottom portion 144 of the container 102 rests on the bottom plate 618. Thus, because the bottom plate 618 supports the container 102 in this embodiment (and the embodiment of FIG. 5), the holder 602 may be mounted only to (or on) a vertical surface 192, such as a wall or mirror, without the bottom plate 618 sitting on or contacting a platform 190, such as a counter. The transverse plate 610 is thus connected to the attachment member 608 at a back of the dispenser 600 and to the front plate 616 at a front of the dispenser 600.

To replace a depleted supply of mouthwash 106, the stem 114 may be pulled or tilted away from the stem support 604 and the attachment member 608 through the slot 612. Once the stem 114 is removed from, or clear of, the slot 612 in the stem support 604, the container 102 and pump 108 may be lifted such that the bottom portion 144 of the container 102 is removed from the hole 614 in the transverse plate 610. As described previously, after the container 102 with the pump 108 is removed from the holder 602, the pump 108 may be removed from the container 102 and reused on a new container, or the entire container 102 and pump 108 may be replaced with a new container and pump.

As with the FIG. 5 holder 502, the edges of the transverse plate 610 that define the hole 614 of the holder 602 of FIG. 6 may physically contact the container 102 near the middle portion of the container 102, which is closer to the center of gravity of the container 102 compared to the contact points of the holder 130 of FIG. 1. For implementations of holders that do not include the optional locking mechanism 160, contacting the container 102 at a higher point(s) nearer to its center of gravity may reduce accidental or unwanted forward tipping of the container 102. Additionally, the holder 602 provides a larger attachment member 608 than the attachment member 508 of the FIG. 5 implementation of a holder 502, and may therefore provide a more secure connection to a wall or mirror 192 (FIG. 1). Additionally, because the transverse plate 610 and the attachment member 608 both physically contact or connect to the base 606, the holder 602 may be more stable than the holder 502 of FIG. 5.

In the FIG. 6 structure, the stem support 604 is directly connected to the attachment member 608, the attachment member 608 is directly connected to the transverse plate 610, the transverse plate 610 is directly connected to the front plate 616 of the base 606, and the front plate 616 is directly connected to the bottom plate 618 of the base 606. Additionally, the attachment member 608 is directly connected to the bottom plate 618 of the base 606. In contrast, in FIG. 5, the attachment member 508 is not directly connected to the bottom plate 518 of the base 506, but rather is indirectly connected to the bottom plate 518 through the transverse plate 510 and the front plate 516.

Additionally, a height of the attachment member 608 is designed such that a distance from the underside of the stem support 604 to the top of the bottom plate 618 is essentially equal to a distance from a bottom horizontal surface of the container 102 to a top surface of the collar 116. This, along with a locking mechanism, assists in preventing the container 102 from being removed from the holder 602 and prevents the collar 116 of the pump 108 from being unscrewed or otherwise removed from the container 102, and prevents removal of the container 102 and pump 108 from the holder 602.

In various implementations, the container holder 130, 502, 602, may have a height of from about 5 inches to about 11 inches, a width of from about 3 inches to about 5 inches, and a depth of from about 1.5 inches to about 3 inches.

Figure 7:
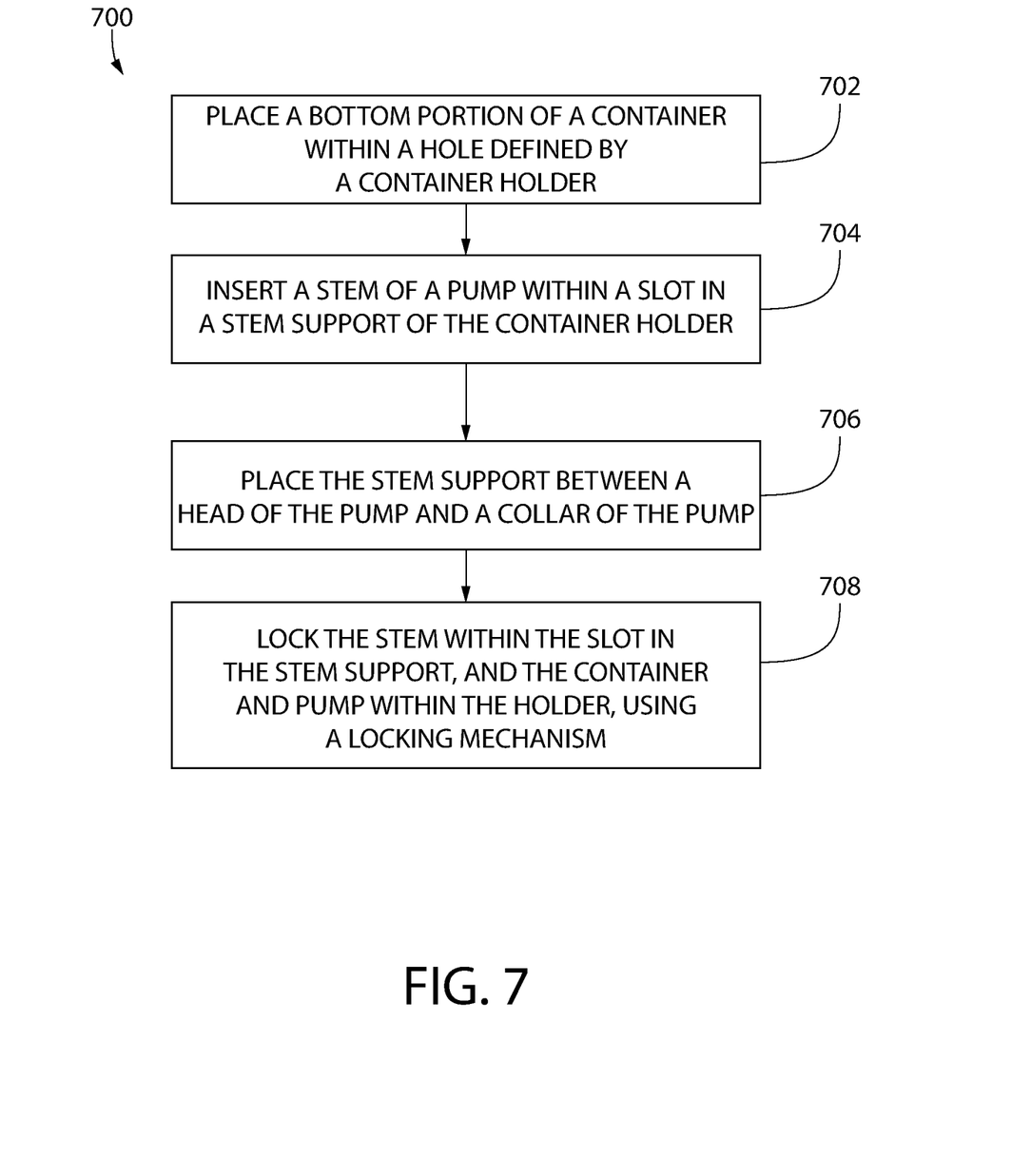
FIG. 7 is a flow chart of a method in accordance with an implementation of the present teachings.

FIG. 7 is a flow chart depicting an example of a method 700 for storing and/or dispensing a volume of fluid, such as mouthwash, in accordance with an implementation of the present teachings. The method 700 may proceed by operation or use of one or more of the structures depicted in the figures described above, and thus is described with reference to FIGS. 1 and 2; however, it will be appreciated that the method 700 is not limited to any particular structure unless expressly stated herein.

The method begins at 702, where a bottom portion 144 of a container 102 is placed or positioned within a hole 142 defined by a container holder 130. At 704, a stem 114 of a pump 108 is inserted or positioned within a slot 138 in a stem support 132 of the container holder 130. The stem support 132 may be place or positioned between a head 110 of the pump 108 and a collar 116 of the pump 108 as described at 706. The stem 114 may be locked within the slot 138 in the stem support 132, which also locks the container 102 and the pump 108 within the holder 130, using a locking mechanism as described at 708. The locking mechanism may include any one of locking mechanisms depicted in FIGS. 2-4, or another locking mechanism.

Figure 8:
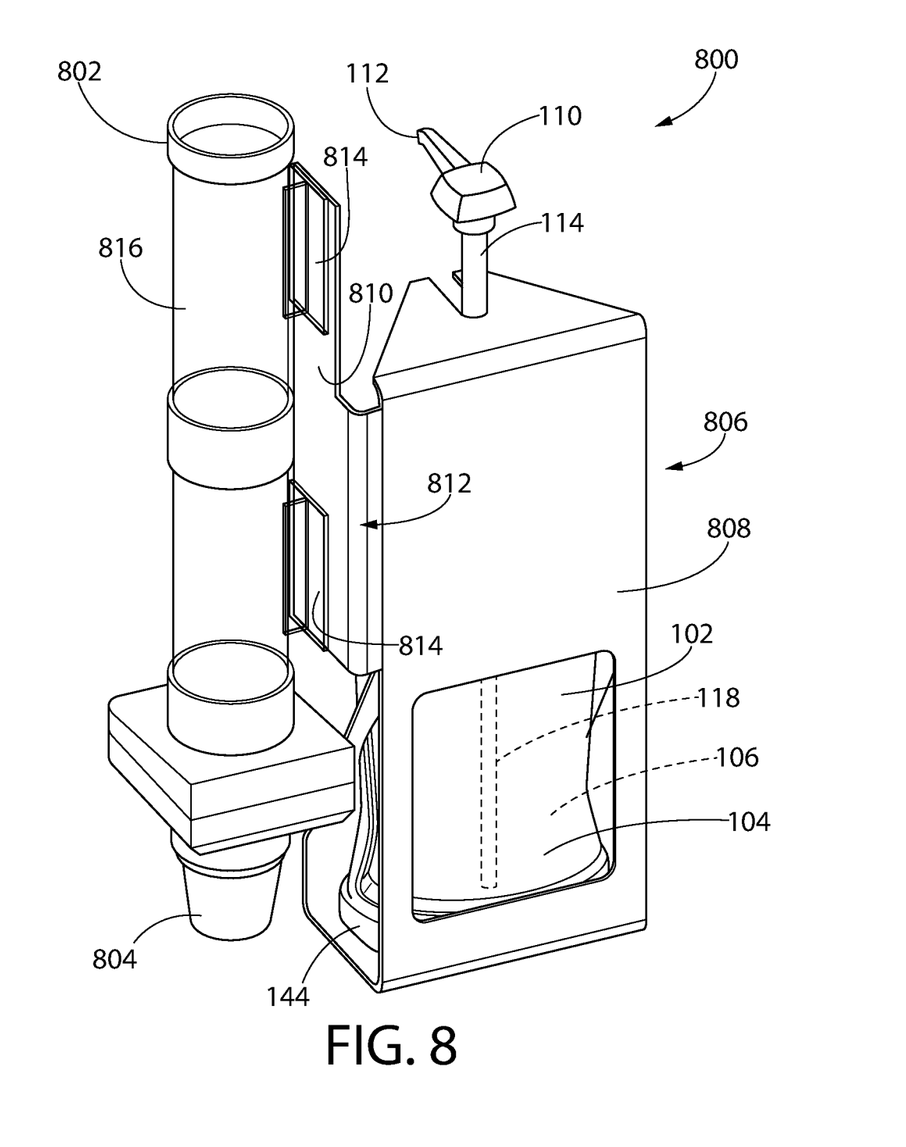
FIG. 8 is a perspective depiction of a fluid dispenser including a cup dispenser in accordance with another implementation of the present teachings.

FIG. 8 depicts a mouthwash dispenser 800 having a design that includes a cup dispenser 802 for dispensing one or more cups 804 in accordance with another implementation of the present teachings. As depicted in FIG. 8, a holder 806 includes an attachment member 808 and an accessory plate 810. During formation of the holder 806, the attachment member 808 and the accessory plate 810 may be formed to be coplanar and, subsequently, the holder 806 may be bent along a joint 812 at a location between the attachment member 808 and the accessory plate 810. Alternatively, the accessory plate 810 may be formed with the bend at the joint 812, for example, in an injection molding process. The dimensions of the accessory plate 810 may be determined, at least in part, by the size, shape, and/or weight of the cup dispenser 802.

FIG. 8 further depicts the cup dispenser 802 attached to the accessory plate 810 using one or more fasteners or anchors 814. The accessory plate 810 thus provides a structure to which the cup dispenser 802 may be attached or anchored. The one or more anchors 814 may include a double-sided pressure-sensitive adhesive, glue, screws, bolts, rivets, clips or other materials.

The cup dispenser 802 may include a vertically oriented cup receptacle 816 for storing a supply of cups 804. Various designs of cup dispensers 802 are contemplated.

As depicted in FIG. 8, the bend along the joint 812 may be a 90° bend such that the accessory plate 810 is positioned perpendicular or at a right angle relative to the attachment member 808, although other angles are contemplated depending on the design of the holder 806.

In another implementation, the accessory plate 810 may remain coplanar with the accessory plate 808. In other words, the joint 812 has no bend and a plane of the accessory plate remains coplanar with a plane of the attachment member 808. In this implementation, the cup dispenser 802 may be attached to the opposite side of the accessory plate 810 from that depicted in FIG. 8.

The present teachings are discussed herein relative to an exemplary mouthwash dispenser and a container holder that holds and positions a mouthwash container. It will be appreciated that the disclosure may be applied to other fluids to provide another type of fluid dispenser having a container holder, where the fluid dispenser stores and dispenses a fluid other than mouthwash. For example, the container holder as described above may be used with personal care product (e.g., shampoo, conditioner, body wash, liquid hand soap, lotion, etc.) containers and/or home care product (e.g., household cleaner, dish liquid, etc.) containers.

While the present teachings have been illustrated with respect to one or more implementations, alterations and/or modifications can be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects of the present teachings. It will be appreciated that structural components and/or processing stages can be added or existing structural components and/or processing stages can be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. As used herein, the term "one or more of" with respect to a listing of items such as, for example, A and B, means A alone, B alone, or A and B. The term "at least one of" is used to mean one or more of the listed items can be selected. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "conformal" describes a coating material in which angles of the underlying material are preserved by the conformal material. The term "about" indicates that the value listed may be somewhat altered, as long as the alteration does not result in nonconformance of the process or structure to the described teachings. Finally, "exemplary" indicates the description is used as an example, rather than implying that it is an ideal. Other aspects of the present teachings will be apparent to those skilled in the art from consideration of the specification and practice of the disclosure herein. It is intended that the specification and examples be considered as exemplary only, with a true scope and spirit of the present teachings being indicated by the following claims.

Terms of relative position as used in this application are defined based on a plane parallel to the conventional plane or working surface of a workpiece, regardless of the orientation of the workpiece. The term "horizontal" or "lateral" as used in this application is defined as a plane parallel to the conventional plane or working surface of a workpiece, regardless of the orientation of the workpiece. The term "vertical" refers to a direction perpendicular to the horizontal. Terms such as "on," "side" (as in "sidewall"), "higher," "lower," "over," "top," and "under" are defined with respect to the conventional plane or working surface being on the top surface of the workpiece, regardless of the orientation of the workpiece.

What is claimed is:

1. A fluid dispenser for dispensing a fluid, comprising:
   a container having an internal reservoir for containing a volume of the fluid;
   a fluid pump received by the container, the fluid pump comprising:
     a head;
     a spout;
     a stem; and
     a collar, wherein the collar attaches the fluid pump to the container; and
   a container holder comprising:
     a stem support that defines a slot that receives the stem of the fluid pump, where the slot is configured for insertion of the stem into the slot in a lateral direction;
     a base comprising:
       a first surface having a hole extending therethrough that receives a bottom portion of the container; and
       a second surface that extends away from the first surface, wherein:
         the bottom portion of the container extends through the hole in the first surface and is configured to physically contact a platform upon which the fluid dispenser is positioned during use; and
         the first surface is supported by the second surface and is configured to be free from physical contact with the platform upon which the fluid dispenser is positioned during use; and
     an attachment member extending from the stem support toward the base.

2. The fluid dispenser of claim 1, wherein a height of the attachment member is designed such that a distance from an underside of the stem support to a bottom edge of the second surface is essentially equal to a distance from a bottom surface of the container to a top surface of the collar.

3. The fluid dispenser of claim 1, wherein:
   the second surface extends approximately perpendicular to the first surface;
   the stem support is directly connected to the attachment member;
   the attachment member is directly connected to the first surface of the base; and
   the first surface of the base is directly connected to the second surface of the base.

4. The fluid dispenser of claim 1, wherein:
   the stem support further comprises a recess therein; and
   the fluid dispenser further comprises an insert configured to be received by the recess in the stem support such that the insert blocks the slot of the stem support.

5. The fluid dispenser of claim 1, wherein:
   the stem support further comprises a recess therein; and
   the fluid dispenser further comprises a locking mechanism, the locking mechanism comprising:
     an insert configured to be received by the recess in the stem support such that the insert blocks the slot of the stem support; and
     a closure that extends through the insert and the stem support.

6. The fluid dispenser of claim 1, wherein:
   the stem support further comprises a recess therein; and
   the fluid dispenser further comprises a locking mechanism, the locking mechanism comprising:
     an insert configured to be received by the recess in the stem support such that the insert blocks the slot of the stem support;
     a post that extends through the stem support and the insert;
     a lock portion that receives the post; and
     a key configured to be inserted into the lock portion to lock and unlock the lock portion from the post.

7. The fluid dispenser of claim 1, further comprising:
   an arm comprising a first end, a second end opposite the first end, and a void within the second end;
   a channel that extends through the stem support and first end of the arm;
   a spindle extending through the channel that attaches the first end of the arm to the stem support, wherein the arm is rotatable about the spindle;
   the stem support further comprises a protrusion, where the void is configured to receive the protrusion; and
   the arm is configured to block the slot in the stem support when the protrusion is positioned within the void in the arm.

8. The fluid dispenser of claim 1, further comprising a volume of mouthwash or mouth rinse contained within the internal reservoir of the container.

9. The fluid dispenser of claim 1, wherein the container holder is formed from a single continuous piece of material comprising at least one of a polymer and a metal.

10. The fluid dispenser of claim 1, wherein the container holder is a single continuous piece of injection-molded polymer.

11. A container holder for holding a container, the container holder comprising:
    a stem support that defines a slot configured to receive a stem of a fluid pump, where the slot is configured for insertion of the stem into the slot in a lateral direction;
    a base;
    an attachment member extending from the stem support toward the base;
    a first surface having a hole extending therethrough that receives a bottom portion of a container; and
    a second surface that extends away from the first surface, wherein:
      the hole is configured such that the bottom portion of the container extends through the hole and physically contacts a platform upon which the fluid dispenser is positioned during use; and
      the first surface is supported by the second surface and is configured to be free from physical contact with the platform upon which the fluid dispenser is positioned during use.

12. The container holder of claim 11, wherein:
    the stem support further comprises a recess therein; and
    the container holder further comprises an insert configured to be received by the recess in the stem support such that the insert blocks the slot of the stem support.

* * * * *